United States Patent [19]
Holme et al.

[11] Patent Number: 5,248,506
[45]' Date of Patent: * Sep. 28, 1993

[54] SYNTHETIC, PLASMA-FREE, TRANSFUSIBLE STORAGE MEDIUM FOR RED BLOOD CELLS AND PLATELETS

[75] Inventors: Stein Holme, Virginia Beach; William A. L. Heaton, Norfolk, both of Va.

[73] Assignee: American National Red Cross, Washington, D.C.

[*] Notice: The portion of the term of this patent subsequent to Oct. 9, 2007 has been disclaimed.

[21] Appl. No.: 593,932

[22] Filed: Oct. 5, 1990

Related U.S. Application Data

[63] Continuation-in-part of Ser. No. 99,012, Sep. 21, 1987, Pat. No. 4,961,928, which is a continuation-in-part of Ser. No. 841,435, Mar. 19, 1986, Pat. No. 4,695,460.

[51] Int. Cl.⁵ .............................................. A61K 35/18
[52] U.S. Cl. .................................. 424/533; 424/529; 424/532; 435/2
[58] Field of Search ............................ 435/2; 424/533

[56] References Cited

U.S. PATENT DOCUMENTS 4,695,460 9/1987 Holme .................................. 424/532
4,961,928 10/1990 Holme .................................... 435/2

Primary Examiner—Sam Rosen
Attorney, Agent, or Firm—Levy, Zito & Grandinetti

[57] ABSTRACT

The invention is a sterile, plasma-free storage medium for blood components including red blood cells and for platelets processed separately or together. The red cell storage medium includes a physiologically compatible, aqueous electrolyte solution. In one liter of this electrolyte solution there is between about 3.0 grams and about 25.0 grams of dextrose, between about 3.0 grams and about 6.0 grams of sodium citrate, and between about 2.0 grams and about 4.2 grams of sodium bicarbonate. The red cell storage medium is isotonic and has a pH in a range of between about 6.8 and about 7.4. The red cell storage medium is capable of storing and preserving red cells for at least 49 days.

14 Claims, 2 Drawing Sheets

SYNTHETIC, PLASMA-FREE, TRANSFUSIBLE STORAGE MEDIUM FOR RED BLOOD CELLS AND PLATELETS

This is a continuation-in-part of U.S. patent application Ser. No. 07/099,012, filed Sep. 21, 1987, which is now U.S. Pat. No. 4,961,928, issued Oct. 9, 1990, which was a continuation-in-part of U.S. patent application Ser. No. 06/841,435 filed Mar. 19, 1986 now U.S. Pat. No. 4,695,460, issued Sep. 22, 1987.

BACKGROUND OF THE INVENTION

1. Technical Field

The present invention relates to a synthetic, plasma-free suspension medium for red blood cells and platelets. More particularly, the present invention relates to a synthetic preservation medium for red blood cells or platelets which (1) is free of blood plasma and other proteins, (2) extends red blood cell or platelet shelf life while maintaining the quality of concentrates of these components during storage for transfusion and (3) is free of unessential organic compounds.

2. State of the Art

Blood is composed of two major portions. These portions can be recognized when a specimen of blood is drawn and clotting is prevented. That portion of the blood which settles to the bottom of the vessel holding the specimen is termed the "formed elements." The formed elements comprise red blood cells and other particulate components such as white blood cells, red blood cells, and platelets. Platelets are also known as thrombocytes. The formed elements are characteristically 40 to 50 percent of the bulk of normal human blood. The cloudy liquid which does not settle in a blood specimen is the portion of the blood known as plasma. Plasma is primarily water, but contains inorganic and organic substances as well as dissolved gases and miscellaneous foreign substances. The inorganic substances contained in blood plasma are primarily electrolytes. The most significant of these electrolytes are presented in Table 1 in the concentrations typically found in healthy, human blood plasma.

TABLE 1

| | |
|---|---|
| Sodium | 142.0 mEq/l |
| Potassium | 4.3 mEq/l |
| Calcium | 5.0 mEq/l |
| Magnesium | 3.4 mEq/l |
| Chloride | 104.0 mEq/l |
| Bicarbonate | 27.0 mEq/l |
| Phosphate | 2.3 mEq/l |
| Sulfate | 0.6 mEq/l |

The most significant organic substances found in the plasma are lactic acid, urea, amino acids, creatinine, glucose, hormones, proteins, albumins, and globulins.

Modern medicine has been developing solutions that are added to blood in vivo and/or mixed with blood in vitro. Products that are used for adding to blood in vivo are primarily used for intraveneous feeding, pharmaceutical vehicles, and/or electrolyte replacement in patients who are bedfast. These solutions are primarily comprised of water that contains dextrose and, optionally, electrolytes. Dextrose is typically present in these solutions in about a 5 percent concentration and provides a nutrient for blood cells or tissue cells. The electrolytes contained in these solutions vary widely. The solutions that contain electrolytes that most closely resemble blood plasma contain a plurality of the electrolytes presented in Table 1. A specific example of a dextrose and electrolyte solution suitable for in vivo addition in blood is Locke-Ringer's solution. The formula for Locke-Ringer's solution is presented in Table 2.

TABLE 2

| | |
|---|---|
| Reagent Sodium Chloride | 9.0 Gm |
| Reagent Potassium Chloride | 0.42 Gm |
| Reagent Calcium Chloride | 0.24 Gm |
| Reagent Magnesium Chloride | 0.2 Gm |
| Sodium Bicarbonate | 0.5 Gm |
| Dextrose | 0.5 Gm |
| Water, recently distilled from a hard glass flask, in a sufficient quantity, to make | 1000 ml |

Other solutions suitable for the addition of blood in vivo can be found in Remington's Pharmaceutical Sciences, Mack Publishing Company, 14th Edition (1970), pages 815 to 847.

Solutions that are added to blood in vitro are either simple anticoagulant nutrient mixtures principally designed for preserving whole blood or separated components for limited periods of time or are specific nutrient solutions optimized for prolonged preservation of specific blood components such as red cells, platelets, white blood cells, or mixtures of these components. When platelets are included as one component of blood that is to be collected and preserved in vitro with red blood cells, it is desirable to use a less active anticoagulant.

The most frequently used anticoagulant added to collected whole blood is known as "acid citrate-dextrose" or "ACD". This anticoagulant solution contains a mixture of anticoagulant and nutrient specifically; (1) citric acid and sodium citrate in optimum concentrations sufficient to chelate calcium without creating an unphysiological pH; and (2) dextrose in concentrations sufficient for short term preservation of blood or components, especially the red blood cells. A less acidic solution that has been found desirable to preserve both whole blood and other cellular fractions is known as "anticoagulant citrate-phosphate-dextrose solution" or "CPD". The components of anticoagulant citrate phosphate-dextrose solution are presented in Table 3.

TABLE 3

| | |
|---|---|
| Citric Acid (anhydrous) | 3.0 Gm |
| Sodium Citrate (dihydrate) | 26.3 Gm |
| Sodium Biphosphate (monohydrate; $NaH_2PO_4H_2O$) | 2.22 Gm |
| Dextrose | 25.5 Gm |
| Water for Injection, in a sufficient quantity to make | 1000 ml |

Specific elements of the particulate component of blood can be separated and better preserved for later transfusion at different temperatures. Simple separation processes can be used to collect and preserve white blood cells and platelets which are best stored at 22° C. rather than 4° C. which is optional for red cells.

Storage of red cells at 4° C. for transfusion results in deterioration of the cells over a period of time. This deterioration of the cells is termed "storage lesion" and is characterized by increased hemolysis and decreased viability resulting in lowered post-transfusion survival of the red blood cells. The alterations associated with storage lesion include intracellular changes such as decreased potassium ion and increased sodium and calcium ion concentrations, the loss of 2,3-diphosphoglycerate (2,3 DPG) resulting in altered oxygen-transfer characteristics, the depletion of adenosine triphosphate (ATP), and membrane skeleton alterations resulting in decreased deformability and increased fragility.

Red cells were previously, typically stored in a combined nutrient-anticoagulant mixture consisting of 1 part nutrient-anticoagulant to 7 parts plasma (acid-citrate-dextrose). The progression of storage lesion was the limiting factor to the shelf life of stored red cells. The shelf life of stored red blood cells was generally limited to 21 days.

More recently, improved red cell viability with storage periods up to 49 days has been achieved with additives specifically mixed with red cells after the plasma and platelets have been removed. Typically, these additive solutions are a simple saline solution fortified with adenine, glucose, and other, minor constituents that are added to retard development of hemolysis and loss of 2,3 DPG. The primary container used with these additive solutions contains only a simple anticoagulant which for convenience has been CPO as described previously. After collection, the anticoagulated whole blood is centrifuged and the platelet-rich plasma and red blood cells are transferred to a satellite bag. The red cell additive solution is then mixed with the red cells. Mixing the additive solution into the separated red blood cells prevents contamination of other separated components of the blood with the red cell additive solution. Desirable flow properties can be maintained for the red cells by using an appropriate volume of the additive solution.

Numerous additive solutions for red blood cells exist either as commercial or research products. The typical additive solution for red blood cells is derived from a saline-adenine-glucose (SAG) medium. SAG was developed in Sweden in the mid 1970's and provides acceptable erythrocyte survival after 35 days of storage rather than the 21 days that was previously available with combined anti-coagulant nutrient solutions SAG maintains acceptable ATP levels throughout 35 days of storage. The storage of red blood cells for 35 days in SAG results in an average hemolysis of approximately 1 percent by the last day of storage which was much greater than the 0.1 percent normally associated with either CPD or ACD. The increased hemolysis of red blood cells in SAG, when compared to storage in a simple solution of sodium citrate, dextrose, citric acid, monobasic sodium phosphate, which is now fortified with adenine (CPDA-1) for prolonged storage (35 days), is believed to result from the action of either white cell proteases upon the erythrocyte membrane in the absence of plasma proteins or as a result osmotic destabilization due to unphysiological storage solutions.

A modified SAG contains mannitol (29 mM) and is known by the symbol SAG-M. This additive solution results in membrane stabilization and decreased hemolysis. A product having a similar formula to SAG-M is the ADSOL ® brand of storage medium. ADSOL ® which is licensed for commercial use in the United States and contains 50 percent more adenine and 150 percent more glucose in addition to 750 mg/dl of mannitol than does SAG-M. This product is produced by Baxter, Inc., 1425 Lake Cook Road, Deerfield, Ill. 60015. The ingredients of the ADSOL ® brand of storage medium are presented in Table 4.

TABLE 4

| | |
|---|---|
| Dextrose | 2.2 g |
| Sodium Chloride | 900.0 mg |
| Mannitol | 750.0 mg |
| Adenine | 27.0 mg |
| Water in a sufficient quantity to make | 100.0 ml |

The presence of mannitol in the ADSOL ® brand storage medium reduces hemolysis even in the presence of leukocyte proteases. The high concentration of dextrose in the ADSOL ® brand storage medium is believed to have desirable effects on other red blood cell parameters. The ADSOL ® brand storage medium can effectively store red cells for 42 days.

However, there are disadvantages and problems with the current generation of red blood cell storage media. These media are ionically unbalanced with sodium as the only cation. Since the active cation transport system of red blood cells is inhibited at low temperatures, a loss of the normal concentration gradient occurs in the red blood cells due to passive diffusion of the cations. This can cause swelling of the cell and eventual lysis. The addition to these solutions of a membrane-stabilizer or "osmotic agent" such as mannitol or sorbitol can not fully compensate for the environmental perturbation of the red cells in these solutions.

The present generation of red blood cell additive solutions have a limited buffering capacity. These limited buffering systems allow the pH of the red blood cell concentrates to decline to levels below 6.5 after about 42 days of storage at 4° C. At this pH level and below, glycoysis with ATP reduction causes the loss of red blood cell viability during storage. The 2,3 DPG level is also markedly sensitive to a decline in pH during storage. Loss of 2,3 DPG results in altered red blood cell oxygen binding characteristics.

The storage of platelets in special additive solutions is commonly performed in special or "second generation" containers. These containers are more gas permeable than the "first generation" of blood storage containers that are made of polyvinyl chloride (PVC). The use of these special containers allows carbon dioxide ($CO_2$) gas to escape during storage of the blood component. The escape of $CO_2$ gas reduces the formation of carbonic acid in the preservation of storage solution. The reduction of carbonic acid in solution extends the period of time during which a physiologically acceptable pH can be maintained in the storage solution.

U.S. Pat. No. 4,447,415 to Rock et al. discloses a liquid storage medium for platelets that is plasma-free. The medium of this invention uses one or more additives in conjunction with a saline and anticoagulant, dextrose-containing solution that is desirably a form of CPD Tyrode's solution. The additives disclosed as being suitable for use with this invention include (1) reversible inhibitors that are organic compounds such as indomethacin, quinacrine, or vitamin E and (2) substances to raise cyclic adenosine monophosphate levels such as prostaglandins $E_1$, $D_2$, or $I_2$. Many of these additives fail to meet safety and regulatory requirements required for substances for infusion into humans and are, therefore, only suitable for experimental use or only for in vitro use. Other additives disclosed as suitable for use with this invention include (1) nutrients such as fructose and other sugars, adenine, or acetyl CoA and (2) buffers such as phosphate and certain amino acids. The organic compounds or additives identified as nutrients do not eliminate the requirement for the presence of dextrose in the medium. The combination of additive and glucose carried over in the plasma satisfies the nutrient requirement for the platelets for periods of storage time extending up to 5 days and the additives identified as buffers cannot maintain a balanced pH during extended platelet storage periods beyond this time. Since the glucose levels are clearly-inadequate for red cell storage over longer time periods and these buffers cannot adequately buffer the amount of lactic acid produced by viable, suspended red cells stored at temperatures of 4°±2° C. cell death due to pH fall is likely. As a result this solution, though potentially acceptable for platelets, cannot be used to store red cells. This disclosure is, therefore, not directed to a storage medium for red blood cells.

The industry is lacking a blood cell storage additive medium that is free of plasma and organic compounds, which can be used to store red blood cells and platelets for extended periods of time and which is safe for in vivo human use.

SUMMARY OF THE INVENTION

Figure 1:
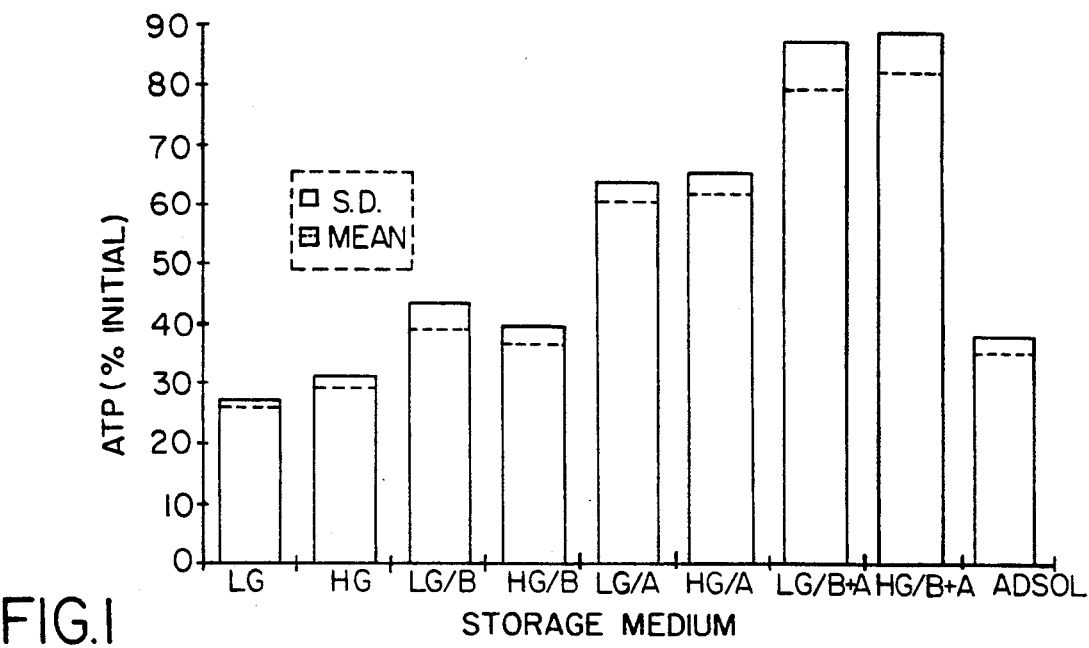
FIG. 1 graphically compares the percent loss of ATP in red blood cells after 49 days of storage in various embodiments of the red blood cell storage medium and a control storage medium.

This invention is a sterile, plasma free storage medium for blood components including red blood cells and/or platelets processed separately or together. The most desirable embodiment of this invention is a sterile, plasma-free red blood cell storage medium. The red blood cell storage medium includes a physiologically compatible, aqueous electrolyte solution In one liter of this electrolyte solution there is between about 3.0 grams and about 25.0 grams of dextrose, between about 3.0 grams and about 6.0 grams of sodium citrate, and between about 2.0 grams and about 4.2 grams of sodium bicarbonate. The red blood cell storage medium is isotonic with the blood to be stored and has a pH in a range of between about 6.8 and about 7.4. The red blood cell storage medium is capable of storing and preserving red blood cells for at least 49 days at a temperature of at least about 4° C. The embodiments of the invention that are most desirable include about 27 mg/dl of adenine.

The red blood cell storage medium can have electrolytes including, in 1 liter of the medium, between about 6.4 grams and about 7.6 grams of sodium chloride, between about 0.2 gram and about 0.4 gram of potassium chloride, between about 0.1 gram and about 0.4 gram of calcium chloride, between about 0.2 gram and about 0.4 gram of magnesium sulphate, and between about 0.1 gram and about 0.6 gram of monobasic sodium phosphate.

The invention also includes a process for preserving red blood cells in a sterile, plasma-free storage medium.

DETAILED DESCRIPTION OF THE INVENTION

This invention is a sterile, plasma-free storage medium for blood components including red blood cells and platelets. The most desirable embodiment of this invention is a sterile, plasma-free red blood cell storage medium. The red blood cell storage medium includes a physiologically compatible, aqueous electrolyte solution. In one liter of this electrolyte solution there is between about 3.0 grams and about 25.0 grams of glucose or more desirably, dextrose, between about 3.0 grams and about 6.0 grams of sodium citrate, and between about 2.0 grams and about 4.2 grams of sodium bicarbonate. The red blood cell storage medium desirably contains an effective concentration of adenine. The red blood cell storage medium is isotonic with human or another blood to be stored and has a pH in a range of between about 6.8 and about 7.4. Except for the nutrient sugar that is desirably dextrose, citric acid or citric acid derivatives, sodium bicarbonate and in certain embodiments, adenine, the red blood cell storage medium of this invention is free of organic compound additives. The term "viable" red blood cells as used herein means that substantial concentrations of the isolated platelets suspended in the red blood cell storage medium retain their normal and inherent physiological, functional, and structural properties such that the stored red blood cells are suitable for infusion and function after infusion in a recipient.

The physiologically compatible, aqueous electrolyte solution of this invention can be varied with only marginal effect on the storage capability of the red blood cell storage medium. The most desirable embodiments of the red blood cell storage medium contain the most significant electrolytes found in blood plasma. The electrolytes are contained in the red blood cell storage medium in the same approximate concentrations as found in normal blood plasma. The most desirable electrolytes include sodium chloride, potassium chloride, calcium chloride, magnesium sulphate, and monobasic sodium phosphate.

Electrolytes, such as those identified above and others, are commonly available in aqueous solutions for injection or infusion into a recipient. In preparing the red blood cell storage medium the concentration of these electrolytes can be altered by known techniques to obtain an isotonic solution. A desirable embodiment of the red blood cell storage medium has electrolytes which include, in 1 liter of the medium, between about 6.4 grams and about 7.6 grams of sodium chloride, between about 0.2 gram and about 0.4 gram of potassium chloride, between about 0.1 gram and about 0.4 gram of calcium chloride, between about 0.2 gram and about 0.4 gram of magnesium sulphate, and between about 0.1 gram and about 0.6 gram of monobasic sodium phosphate.

A desirable storage solution for red blood cells is one that contains electrolytes that most closely resemble blood plasma. An ionic environment simulating protein-free plasma produce less membrane perturbance and hemolysis in stored red blood cells. The more stable membrane improves the normal metabolism of the red blood cells such that ATP and 2,3 DPG are maintained and lactate output is reduced. Normal metabolism lessens the need in storage solutions for special red blood cell additives such as adenine, mannitol, and high glucose.

Glucose in the form of dextrose is the natural nutrient for red blood cells. Dextrose significantly contributes to the ability of the red blood cell storage medium to preserve and maintain viable red blood cells for extended storage periods beyond a 35 day period. The red blood cell storage medium of this invention uses dextrose as the only significant nutrient for the stored red blood cells. An insignificant presence of another nutrient or the use of racemic glucose does not appreciably alter the effectiveness of the red cell storage medium of this invention. The presence of another nutrient is undesirable because other nutrients are not as effective as dextrose in the long term preservation of red blood cells.

The concentration of dextrose in the red cell storage medium of this invention is than the dextrose concentrations typically used in solutions for use with whole blood or blood components. The higher dextrose concentration must be sufficient to provide nutrients for the stored red blood cells throughout their storage period. Dextrose is desirably present in the red cell storage medium in a concentration of at least about 3.0 grams per liter and most desirably at about 7.2 grams per liter. Typically, a concentration of dextrose of between about 4.0 to about 25.0 grams per liter is sufficient to provide red blood cells, stored according to this invention, with sufficient nutrients for at least about 49 days. The concentration of dextrose in embodiments of this invention useful for the storage of platelets is at least about 3.0 grams per liter and desirably between about 3.0 grams and 7.5 grams per liter.

The buffer system of the red cell storage medium of this invention is critical to the successful storage of red blood cells for at least about 49 days. The use of a substantial concentration of sodium bicarbonate to the red cell storage medium neutralizes much of the lactic acid formed during red blood cell storage. The concentration of sodium bicarbonate must be sufficient to maintain a red cell storage medium pH for the stored red blood cells at above about 6.5 throughout the term of the storage period. A red cell storage medium pH value below about 6.5 can be damaging to the stored red blood cells as reflected by in vitro parameters. These in vitro parameters include (1) red blood cell membrane skeleton alterations resulting in decreased deformability and increased fragility or hemolysis, (2) the depletion of ATP, and (3) loss of 2,3 DPG levels resulting in altered oxygen-transfer characteristics. Research has demonstrated that the pH level of the stored red blood cells can be maintained and the 2,3 DPG level stabilized by the addition of a high concentration (110 mM) of sodium bicarbonate to the red cell suspending medium. The use of such a high, nonphysiologic sodium bicarbonate concentration can require the presence of adenine and mannitol in the solution to prevent metabolic and membrane disturbances.

The buffer system of the red cell storage medium of this invention uses sodium bicarbonate as the principal alkaline agent. Sodium bicarbonate is used in concentrations sufficient to maintain the desired pH value of the red cell storage medium throughout red blood cell storage without precipitation of the buffering agent. Desirably, sodium bicarbonate is present in 1 liter of red cell storage medium at a concentration of between about 2.0 grams to about 4.2 grams. The buffer system of the red cell storage medium of this invention desirably includes monobasic sodium phosphate. Minor concentrations of other salts can be suitable for inclusion with the buffering system of this invention.

The anticoagulant used in the red cell storage medium of this invention includes sodium citrate. In the most preferred embodiments of the invention citric acid is included. The anticoagulants of this invention must be present in concentrations sufficient to prevent substantial coagulation of red blood cells during extended storage periods. Desirably, sodium citrate is present in 1 liter of red blood cell storage medium at a concentration of between about 3.0 grams and about 6.0 grams and citric acid is present in 1 liter of red blood cell storage medium at a concentration of between about 0.4 gram and about 0.6 gram. Minor concentrations of other anticoagulants can be suitable for inclusion in the red blood cell storage medium of this invention The red blood cell storage medium of this invention is desirably composed of the chemical ingredients listed in Table 5. The most desirable embodiments of this invention consist essentially of these compounds to the exclusion of a significant concentration of any other compounds. The exclusion of other compounds in the red blood cell storage medium of this invention is desirable in order to prevent sensitization in the recipient and to maximize the storage period for red blood cells.

TABLE 5

|  | Concentration Range | Preferred Concentration |
| --- | --- | --- |
| Sodium Chloride | 6.4–7.6 g/l | 6.450 g/l |
| Potassium Chloride | 0.2–0.4 g/l | 0.375 g/l |
| Calcium Chloride | 0.1–0.4 g/l | 0.248 g/l |
| Magnesium Sulfate | 0.2–0.4 g/l | 0.200 g/l |
| Sodium Phosphate (monobasic) | 0.1–0.6 g/l | 0.355 g/l |
| Dextrose | 3.0–25.0 g/l | 7.2 g/l |
| Citric Acid | 0.4–0.6 g/l | 0.510 g/l |
| Tri-Sodium Citrate | 3.0–6.0 g/l | 4.471 g/l |
| Sodium Bicarbonate | 2.0–4.2 g/l | 3.000 g/l |
| Adenine | 0.26–0.30 g/l | 0.270 g/l |

The individual ionic character of the solution in mEq/l is as follows in Table 6:

TABLE 6

|  | Range of Ionic Concentration | Preferred Ionic Concentration |
| --- | --- | --- |
| $Na^+$ | 198.80–236.10 | 207.60 |
| $K^+$ | 2.68–5.36 | 5.03 |
| $Ca^{++}$ | 1.36–5.45 | 3.38 |
| $Mg^{++}$ | 1.70–3.40 | 1.70 |
| $HPO_4^{-2}$ | 1.38–5.50 | 2.58 |
| $Cl^-$ | 110.00–138.00 | 117.38 |
| $SO_4^{-2}$ | 1.70–3.40 | 1.70 |
| $HCO_3^-$ | 23.80–50.00 | 35.71 |

The pH of the red blood cell storage medium is maintained in the range of between about 6.8 and about 7.4. The pH of the storage medium can vary due to the amount of $CO_2$ present in the container. A high concentration of $CO_2$ lower the pH of the storage medium. The high pH of the storage medium can require separate sterilization of the dextrose from the sodium bicarbonate-containing storage medium because dextrose is not readily sterilized above pH 6.4.

The basic solutions and ingredients suitable for use in making the red cell storage medium of this invention can be obtained from numerous commercial sources as sterile, non-pyrogenic, injectable solutions. Suppliers for the ingredients can be identified from common publications such as the "Physician's Desk Reference" and the "Red Book" each published by the Medical Economics Company Incorporated, Oradell, N.J. The following examples of commercial ingredients are provided as a sampling of acceptable commercial products available for use in this invention Ringer's Injection, USP, contains 8.6 grams of sodium chloride, 0.3 gram of potassium chloride, and 0.33 gram of calcium chloride per liter in sterile, non-pyrogenic water for injection. Sterile water for injection is a non-pyrogenic water for intravenous infusion. Magnesium Sulfate Injection, USP, is a 50 percent solution of magnesium sulphate in sterile, non-pyrogenic water for injection. Sodium bicarbonate injection, USP, is an 8.4 percent solution of sodium bicarbonate in sterile, non-pyrogenic water for injection. Dextrose injection solution, USP, is 50 percent solution of dextrose in sterile, non-pyrogenic water for injection. Potassium Chloride Injection, USP, is a 22 percent solution of potassium chloride in sterile, non-pyrogenic water for injection. Anticoagulant citrate-phosphate-dextrose solution has 3.0 grams of citric acid, 26.3 grams of sodium citrate, 2.22 grams of sodium biphosphate, 25.5 grams of dextrose in one liter sterile, non-pyrogenic water and is used in the proportion of 70 milliliters of CPD to 500 milliliters of whole blood. Adenine is available, from both synthetic and natural sources, as a powder.

The above listed ingredients are combined in the preferred embodiment of the invention in the following amounts. The red cell storage medium solution contains 750 milliliters of Ringer's solution, 170 milliliters of CPD, 40 milliliters of sodium bicarbonate solution, 5.4 milliliters of dextrose injection solution, 0.7 milliliter of potassium chloride, 0.4 milliliter of magnesium sulphate solution, 33.5 milliliters of sterile water for injection, and 270 milligrams of adenine. All ingredients are combined under sterile, aseptic conditions. Prior to innoculation of red blood cells with the red cell storage medium, the mixture of the ingredients is filter sterilized using a 0.2 micron filter unit designed for the vacuum filtration of tissue culture media.

The preferred composition of the red cell storage medium of the present invention and CPD-plasma are compared in Table 7.

TABLE 7

|  | Red Cell Storage Medium mEq/l | CPD-Plasma* mEq/l |
| --- | --- | --- |
| Sodium | 207.60 | 173.0–180.0 |
| Potassium | 5.03 | 1.9–3.8 |
| Calcium | 3.38 | 3.4–4.0 |
| Magnesium | 1.70 | 1.1–1.9 |
| Phosphate | 2.58 | 3.9 |
| Bicarbonate | 40.00 | 20.9 |
| Citrate | 15.00 | 22.4 |
| Sulphate | 1.70 | 0.4–1.1 |
| Chloride | 117.38 | 75.0–80.0 |
| Proteins | 0.0 | 12.2 |
| Organic Acids | 0.0 | 4.4 |
| Citric Acid | 2.60 mmol/l | 3.0 mmol/l |
| Dextrose | 40.00 mmol/l | 25.0 mmol/l |
| Adenine | 2.00 mmol/l | 0.0 mmol/l |

*This concentration assumes that the citrate, citric acid, and phosphate do not enter red cells and is based on a 70 milliliter CPD aniticoagulant solution in 500 milliliters of whole blood having a hematocrit of 42.5 and serum chemical values within the normal limits as listed in Harper's Review of Biochemistry.

After the preparation of the red blood cell storage medium the process for preserving and storing red blood cells requires the separation of red blood cells from the other components of blood. The plasma is "expressed off" and collected in a satellite bag. The red cell storage medium can then be transferred into the container holding the red blood cells. This transfer can be by either connective tubing linking the satellite bag containing the red cell storage medium or commercially available, sterile connection devices that can transfer the medium from a container not originally attached to the collection bag set. After resuspension of the separated red blood cells in the red blood cell storage medium, the red blood cells are stored at 4° C.

Conventional PL-732 red blood cell containers have a high permeability to $CO_2$. Storage of the red blood cells in gas permeable containers such as commercially available, thin polyvinyl chloride (PVC) bags allows the escape of $CO_2$ and, thereby, lessens the need for sodium bicarbonate in the red cell storage medium. This is because the diffusion of $CO_2$ from the container decrease the amount of carbonic acid retained in the contained solution. In platelet storage studies using a platelet container, 40 mM of bicarbonate was sufficient to neutralize 30 mM of lactic acid to achieve a final pH of more than 6.8. A pH of 6.8 can be expected to accumulate at about 42 days of storage of red blood cells at 4° C. The red blood cell storage medium of this invention allows for storage in thin polyvinyl storage containers plasticized with diethylhexylphthalate (DEHP) such as the $CO_2$ permeable containers used for the storage of platelets. These containers lessen the need for sodium bicarbonate because more $CO_2$ gas leaves the container and less carbonic acid is dissolved in the solution. The presence of DEHP as a plasticizer in a container can enhance the quality of stored red blood cells.

In order to demonstrate the suitability of the storage medium of the present invention for preserving blood components, in vitro and in vivo studies were conducted to compare the quality of platelets concentrates stored in the storage medium without the presence of adenine or another membrane stabilizing compound. Examples 1 through 7 with their related Comparative Examples A through I present the results of these tests. In these Examples and Comparative Examples the storage medium was examined for its usefulness in storing platelets and is designated by the terms "Platelet Storage Medium" or "P.S.M."

The following Examples represent the invention. The comparative examples do not represent the invention.

EXAMPLES 1 THROUGH 5 AND COMPARATIVE EXAMPLES A THROUGH E

The procedure used in these examples and comparative examples to separate platelets and to make the storage medium was as described above and in the parent application, now U.S. Pat. No. 4,695,460, for the preferred embodiment of the platelet invention. The data presented for the platelet storage medium is designated by the symbol "P.S.M." and represents Examples 1 through 5 (designated by the symbol "Ex.") for the invention. The data presented for the storage of platelets in CPD-plasma is designated by the symbol "CPD-pl." and represents Comparative Examples (designated by the symbol "C.Ex.") A through E.

For these examples and comparative examples platelets were separated, stored in their respective media, and tested on days 1, 5, 10, and 14. The tests conducted on these days for platelet count determined a percent of the platelet count of the first day, the percent increase in optical density (O.D.) of the extent of platelet shape change with ADP, the percent of hypotonic shock respones, the concentration of adenosine triphosphate or "ATP" in the platelets, and the amount of lysis as evidenced by lactate dehydrogenase or "LDH" released by the platelets. The results of these tests are respectively presented in Tables 8 through 12.

TABLE 8

Platelet Count, % of Day 1*

|  |  | Day 1 | Day 5 | Day 10 | Day 14 |
|---|---|---|---|---|---|
| Ex. 1 | P.S.M. | 100 | 94 ± 3 | 91 ± 2 | 82 ± 4 |
| C. Ex. A | CPD-pl. | 100 | 94 ± 3 | 84 ± 6 | 77 ± 3 |

TABLE 9

Extent of Shape Change, % Increase in O.D.*

|  |  | Day 1 | Day 5 | Day 10 | Day 14 |
|---|---|---|---|---|---|
| Ex. 2 | P.S.M. | 16 ± 1 | 14 ± 1 | 10 ± 1 | 7 ± 1 |
| C. Ex. B | CPD-pl. | 16 ± 1 | 11 ± 1 | 5 ± 1 | 4 ± 1 |

TABLE 10

Hypotonic Shock Response, %*

|  |  | Day 1 | Day 5 | Day 10 | Day 14 |
|---|---|---|---|---|---|
| Ex. 3 | P.S.M. | 75 ± 6 | 65 ± 4 | 63 ± 5 | 40 ± 3 |
| C. Ex. C | CPD-pl. | 82 ± 3 | 78 ± 5 | 49 ± 2 | 12 ± 5 |

TABLE 11

ATP, nmoles/$10^{11}$ plts.*

|  |  | Day 1 | Day 5 | Day 10 | Day 14 |
|---|---|---|---|---|---|
| Ex. 4 | P.S.M. | 8.5 ± 0.4 | 7.7 ± 0.3 | 5.4 ± 0.4 | 3.1 ± 0.4 |
| C. Ex. D | CPD-pl. | 7.5 ± 0.7 | 6.0 ± 0.4 | 3.5 ± 0.3 | 0.8 ± 0.2 |

TABLE 12

LDH, Units Released*

|  |  | Day 1 | Day 5 | Day 10 | Day 14 |
|---|---|---|---|---|---|
| Ex. 5 | P.S.M. | 138 ± 16 | 177 ± 22 | 305 ± 33 | 430 ± 43 |
| C. Ex. E | CPD-pl. | 120 ± 8 | 215 ± 15 | 430 ± 23 | 585 ± 35 |

*Results represent the mean ± standard deviation.

The results of these comparative studies demonstrate that the platelets stored in the platelet storage medium showed better maintenance of morphologic and physiologic integrity as indicated by the following. The platelets suspended in the platelet storage medium of this invention demonstrated a better preservation as evidenced by the differences in platelet count over the period of testing. A decrease in platelet count reflects platelet clumping and/or lysis. The platelets suspended in the platelet storage medium of this invention demonstrated a better maintenance of the ability of the platelets to undergo shape change or to become activated by using physiologic activators. The platelets suspended in the platelet storage medium of this invention demonstrated a better preservation than the platelets suspended in CPD-plasma by their ability to recover from hypotonic stress. The platelets suspended in the platelet storage medium of this invention demonstrated a better maintenance of the ATP levels which reflects the energy status of the platelet cell. The platelets suspended in the platelet storage medium of this invention demonstrated a better maintenance of membrane integrity as indicated by less loss of intracellular LDH during storage.

These examples and comparative examples demonstrate that storage of platelet concentrates in the platelet storage medium for at least 10 to 14 days at nonfreezing temperatures or a temperature of at least about 22° C. maintain in vitro quality that is reflective of in vivo viability, similar to that obtained with storage of platelets in CPD plasma for 5 t 10 days.

EXAMPLE 6

COMPARATIVE EXAMPLES F THROUGH H

This example and comparative examples use the same procedure as described for Examples 1 through 5 and Comparative Examples A through E. This example and comparative examples demonstrate the effect of using various amounts of sodium citrate, sodium chloride, magnesium sulphate, sodium. diphosphate, sodium bicarbonate, $pCO_2$ tensions, dextrose, and plasma in different platelet storage media. These modifications were demonstrated by comparing effects of different platelet storage media over a 10 day storage period on (1) platelet count, (2) the percent of hypotonic shock response, (3) the structural integrity of the platelets characterized by change in size distribution, appearance of platelet clumps, balloon forms, fragments as judged by microscopy, and LDH release, (4) platelet function as characterized by the extent of shape change with ADP, and (5) platelet energy metabolism or the rate of oxygen uptake, lactate production, glucose consumption, and ATP levels. The data demonstrating these characteristics are presented respectively in Tables 13 through 17.

Example 6 presents data for the five characteristics for the platelet storage medium of this invention and is designated by the symbol "P.S.M.".

The comparative examples present data for the five characteristics for the platelet storage media designated by the symbols "BSM", "BSM+glucose", and "DMSM". The symbol "BSM" represents a storage medium having the same characteristics of the preferred platelet storage medium of the platelet invention, but does not contain dextrose and has a lower sodium chloride concentration of 5.23 grams per liter. The symbol "BSM+dextrose" represents a storage medium having the same characteristics of the preferred platelet storage medium of the platelet invention, including dextrose, but has the lower sodium chloride concentration of 5.23 grams per liter. The symbol "DMSM" represents a storage medium having the same characteristics of the preferred platelet storage medium, but does not contain dextrose. The comparative examples do not represent the invention.

TABLE 13

Platelet Count in % of Count at Day 1*

|  |  | Day 1 | Day 5 | Day 10 |
|---|---|---|---|---|
| C. Ex. F | BSM |  | 66 ± 8 | 47 ± 11 |
| C. Ex. G | BSM + dextrose |  | 83 ± 8 | 73 ± 10 |
| C. Ex. H | DMSM |  | 82 ± 10 | 56 ± 9 |
| Ex. 6 | P.S.M. |  | 95 ± 2 | 91 ± 3 |

TABLE 14

Hypotonic Shock Response, % Recovery*

|  |  | Day 1 | Day 5 | Day 10 |
|---|---|---|---|---|
| C. Ex. F | BSM | 28 ± 5 | 20 ± 6 | 4 ± 10 |
| C. Ex. G | BSM + dextrose | 44 ± 10 | 44 ± 10 | 22 ± 10 |
| C. Ex. H | DMSM | 75 ± 13 | 41 ± 10 | 8 ± 5 |
| Ex. 6 | P.S.M. | 73 ± 20 | 61 ± 13 | 51 ± 6 |

TABLE 15

| | | ADP-Shape Change % Increase in O.D.* | | |
|---|---|---|---|---|
| | | Day 1 | Day 5 | Day 10 |
| C. Ex. F | BSM | 13 ± 2 | 7 ± 3 | 2 ± 2 |
| C. Ex. G | BSM + dextrose | 16 ± 3 | 10 ± 4 | 5 ± 3 |
| C. Ex. H | DMSM | 15 ± 3 | 8 ± 2 | 1 ± 1 |
| Ex. 6 | P.S.M. | 17 ± 4 | 14 ± 2 | 10 ± 3 |

TABLE 16

| | | Rate of Oxygen Consumption nmoles/min/$10^9$ plts* | | |
|---|---|---|---|---|
| | | Day 1 | Day 5 | Day 10 |
| C. Ex. F | BSM | 1.0 ± 0.1 | 0.5 ± 0.3 | 0.3 ± 0.1 |
| C. Ex. G | BSM + dextrose | 1.0 ± 0.3 | 0.6 ± 0.1 | 0.6 ± 0.2 |
| C. Ex. H | DMSM | 0.9 ± 0.3 | 0.6 ± 0.1 | 0.2 ± 0.1 |
| Ex. 6 | P.S.M. | 1.0 ± 0.1 | 0.7 ± 0.1 | 0.4 ± 0.3 |

TABLE 17

| | | ATP, nmoles/$10^9$ plts* | | |
|---|---|---|---|---|
| | | Day 1 | Day 5 | Day 10 |
| C. Ex. H | DMSM | 7.1 ± 1.5 | 5.3 ± 2.2 | 0.7 ± 0.2 |
| Ex. 6 | PSM | 8.5 ± 1.5 | 8.4 ± 1.3 | 6.5 ± 0.8 |

*Results represent mean ± standard deviation.

The results of this example and comparative examples demonstrate the following.

(1) A minimum of 3000 to 6000 milligrams per liter of sodium citrate was essential to avoid platelet clumping and subsequent deterioration of the platelets.

(2) Good maintenance of platelet discoid morphology and negligible clumping was obtained with sodium chloride in the concentration range of 64000 to 76000 milligrams per liter. Poor quality of the platelet concentrate was observed in the data of Table 13 with sodium chloride at a concentration of 5.23 grams per milliliter.

(3) The addition of divalent cations ($Mg^{++}$ and $Ca^{++}$) was necessary for maintenance of platelet discoid morphology. Calcium chloride can be used in the concentration range of 100 to 400 milligrams per liter and magnesium chloride can be used in the range of 200 to 400 milligrams per liter with good results.

(4) Potassium chloride was essential to maintain normal morphology and was used in the concentration range of 220 to 400 milligrams per liter with good results.

(5) Sodium diphosphate was used in the concentration range of 100 to 580 milligrams per liter with good results.

(6) Sodium bicarbonate was used in the the concentration range of 2900 to 4200 milligrams per liter with good results. A minimum of 2900 milligrams per liter was found to be necessary in order to prevent a decrease in pH with storage beyond seven days.

(7) A 2.5 to 7.5 percent carbon dioxide atmosphere, depending on the amount of sodium bicarbonate added, was successfully used to maintain a constant pH.

(8) The addition of glucose (dextrose) was essential for maintenance of good in vitro quality of the platelets as evidenced by the data of Table 13. Dextrose was used in the concentration range of 3000 to 7500 milligrams per liter with good results.

(9) The pH of the platelet storage medium was maintained in the range of 6.8 to 7.4 as measured at 22° C. A pH above 7.4 resulted in clumping of the platelets while a pH below 6.8 caused swelling and loss of discoid morphology.

EXAMPLE 7 AND COMPARATIVE EXAMPLE I

The similarity in chemical and physiological attributes of the platelet storage medium to CPD-plasma are indicative of the inherent non-toxic and safe utility characteristics of the platelet or red blood cell storage mediums for infusion into patients. Hence, in vivo study of platelets preserved with the platelet storage medium of this invention was conducted. The studies described herein encompassed 10 paired studies. The paired studies using normal males over the age of 21 not known to have mental or physical disability and not receiving drug therapy. The volunteers donated one unit of platelet, rich plasma which was drawn using the conventional platelet apheresis techniques. This procedure was performed twice. The platelet concentrate was processed for storage for a 7 day period at 22° C. either in CPD plasma or in the red cell storage medium using currently licensed procedure.

Platelet concentrates were stored in an agitator/incubator at about 22° C. The platelet concentrates in CPD-plasma were stored in an ordinary air atmosphere. The platelet concentrates in the platelet storage medium were stored under a 7.5 percent $CO_2$ atmosphere. This processing and storage of platelet concentrates in CPD plasma is consistent with the currently licensed procedure.

The in vivo viability of the platelets was determined by the conventional percent recovery and survival parameters using radioisotopic labeling techniques well known in the art such as discussed in "Platelet Kinetics and Imaging", Volume I, Techniques and Normal Platelet Kinetics, Heyns et al., CRC Press Inc., Boca Raton, Fla. (1985).

At the completion of 7 days of storage, 10 milliliters of platelet concentrate were taken for radioisotopic labeling of the platelets with 111 Indium-Oxine. The washed and labeled platelets were resuspended in 6 milliliters of nonradioactive autologous plasma for infusion into the original donor Two milliliters of blood samples were drawn from the donors at 1, 2, and 3 hour intervals after infusion and then daily thereafter for 7 days for calculation of in vivo percent recovery and survival. The study was designed such that during the first session 5 donor were infused with platelets stored in the platelet storage medium of this invention and 5 donors were infused with platelets stored in CPD plasma. This was repeated during the second session, 2 months later, with the storage medium being reversed for the donors. The percent recoveries and survivals were determined using the gamma function multiple hit program. Paired t-tests were used to detect significant differences. The in vitro viability of the platelets was evaluated by hypotonic shock response and extent of shape change with ADP. The results of the percent of in vivo recovery and survivals are shown in Tables 18 and 19, respectively.

TABLE 18

| | IN VIVO Recovery % | |
|---|---|---|
| Donor | C. Ex. I CPD-plasma | Ex. 7 P.S.M. |
| 1 | 29 | 57 |
| 2 | 23 | 52 |
| 3 | 36 | 52 |
| 4 | 43 | 47 |
| 5 | 31 | 52 |
| 6 | 61 | 66 |
| 7 | 33 | 48 |

TABLE 18-continued

| | IN VIVO Recovery % | |
|---|---|---|
| Donor | C. Ex. I CPD-plasma | Ex. 7 P.S.M. |
| 8 | 28 | 37 |
| 9 | 41 | 44 |
| 10 | 43 | 55 |
| mean ± standard deviation | 37 ± 11 | 51 ± 8 |

TABLE 19

| | Survivals, Hours | |
|---|---|---|
| Donor | C. Ex. I CPD-plasma | Ex. 7 P.S.M. |
| 1 | 54 | 125 |
| 2 | 85 | 162 |
| 3 | 126 | 159 |
| 4 | 171 | 145 |
| 5 | 103 | 155 |
| 6 | 86 | 146 |
| 7 | 122 | 150 |
| 8 | 107 | 114 |
| 9 | 129 | 154 |
| 10 | 121 | 130 |
| mean ± standard deviation | 110 ± 32 | 144 ± 16 |

Mean percent in vivo recoveries and survivals were found to be substantially higher with platelet concentrates stored in red cell storage medium or 51±8 percent and 144±16 hours versus 37±11 percent and 110±32 hours for platelet concentrate stored in CPD-plasma, respectively. The differences were statistically, highly significant as witnessed by a t-test value of $P < 0.005$. The in vitro viability results paralleled the in vivo results as evidenced by the data presented in Tables 20 and 21 with statistically superior results indicated by the paired t-test value of $p < 0.01$ for platelet concentrates stored in platelet storage medium.

TABLE 20

| | Hypotonic Shock Response, % Recovery | |
|---|---|---|
| Donor | C. Ex. I CPD-plasma | Ex. 7 P.S.M. |
| 1 | 18 | 75 |
| 2 | 39 | 57 |
| 3 | 47 | 62 |
| 4 | 40 | 60 |
| 5 | 35 | 58 |
| 6 | 44 | 70 |
| 7 | 47 | 67 |
| 8 | 40 | 50 |
| 9 | 50 | 55 |
| 10 | 77 | 100 |
| mean ± standard deviation | 44 ± 15 | 65 ± 14 |

TABLE 21

| | Extent of Shape Change with ADP | |
|---|---|---|
| Donor | C. Ex. I CPD-plasma | Ex. 7 P.S.M. |
| 1 | 4 | 12 |
| 2 | 6 | 13 |
| 3 | 8 | 19 |
| 4 | 7 | 14 |
| 5 | 10 | 13 |
| 6 | 8 | 14 |
| 7 | 17 | 18 |
| 8 | 7 | 11 |

TABLE 21-continued

| | Extent of Shape Change with ADP | |
|---|---|---|
| Donor | C. Ex. I CPD-plasma | Ex. 7 P.S.M. |
| 9 | 14 | 11 |
| 10 | 19 | 17 |
| mean ± standard deviation | 9 ± 4 | 14 ± 3 |

The results of this example and comparative example indicate that the in vivo viability of platelet concentrates are substantially improved in the platelet storage medium of this invention when compared to platelet storage in CPD-plasma.

EXAMPLES 8 THROUGH 15 AND COMPARATIVE EXAMPLE J

The procedure used in these examples and this comparative example to separate red blood cells from whole blood and to make the storage medium are the same as those described above. Examples 8 through 15 are directed to the red blood cell storage medium of the invention. Comparative Example J demonstrates the current state of the art in red blood cell storage mediums. Comparative Example J uses the red blood cell storage medium sold under the mark ADSOL ®.

Examples 8 through 15 and Comparative Example J were performed with 10 whole blood units collected into CPD anticoagulant and divided aseptically into four subunits to obtain 40 total test units. The blood was collected in 150 milliliter Fenwal PL-146 plastic transfer packs. After the blood was centrifuged, a sufficient quantity of a filtered, sterile storage medium was injected to produce a final hematocrit of 60±5 percent.

Example 8 is directed to the storage of red blood cells with the red blood cell storage medium of this invention having a low glucose (LG) concentration of 7 grams of dextrose per liter.

Example 9 is directed to the storage of red blood cells with the red blood cell storage medium of this invention having a high glucose (HG) concentration of 20 grams of dextrose per liter.

Example 10 is directed to the storage of red blood cells with the red blood cell storage medium of this invention having the low glucose concentration of Example 8 and 2.5 grams (30mM) of sodium bicarbonate (LG/B).

Example 11 is directed to the storage of red blood cells with the red blood cell storage medium of this invention having the high glucose concentration of Example 9 and 2.5 grams (30mM) of sodium bicarbonate (HG/B).

Example 12 is directed to the storage of red blood cells with the red blood cell storage medium of this invention having the low glucose concentration of Example 8 and 270 milligrams of ademine per liter (LG/A).

Example 13 is directed to the storage of red blood cells with the red blood cell storage medium of this invention having the high glucose concentration of Example 9 and 270 milligrams of adenine per liter (HG/A).

Example 14 is directed to the storage of red blood cells with the red blood cell storage medium of this invention having the low glucose concentration of Example 8 with 2.5 grams of sodium bicarbonate and 270 milligrams of adenine per liter (LG/B+A).

Example 15 is directed to the storage of red blood cells with the red blood cell storage medium of this invention having the high glucose concentration of Example 9 with 2.5 grams of sodium bicarbonate and 270 milligrams of adenine per liter (HG/B+A). This represents the preferred embodiment of the red blood cell storage medium.

Comparative Example J is directed to the storage of red blood cells with the red blood cell storage medium sold under the mark ADSOL ® which has 9 grams of sodium chloride, 7.5 grams of mannitol, 22 grams of dextrose, and 270 milligrams of adenine per liter.

Samples of 6 milliliters each of stored red blood cells were drawn in each of the above examples and comparative example for biochemical assay. These samples were drawn immediately after being prepared with the respective storage solutions and on days 7, 14, 21, 35, and 49 of storage at 4° C. The biochemical assays were for determinations of the percent loss of ATP the percent hemolysis, the pH in solution, and the percent loss of 2,3 DPG of the stored red blood cells.

FIGS. 1, 2, 3, and 4 graphically depicts the data of the four biochemical assay described above after the 49 day storage period. These figures present the means, plus or minus a standard deviation, of five studies with each of the eight embodiments of the red blood cell storage medium used in Examples 8 through 15. These data are compared to mean results of 6 subunits of blood stored in the ADSOL ® brand storage medium.

Figure 2:
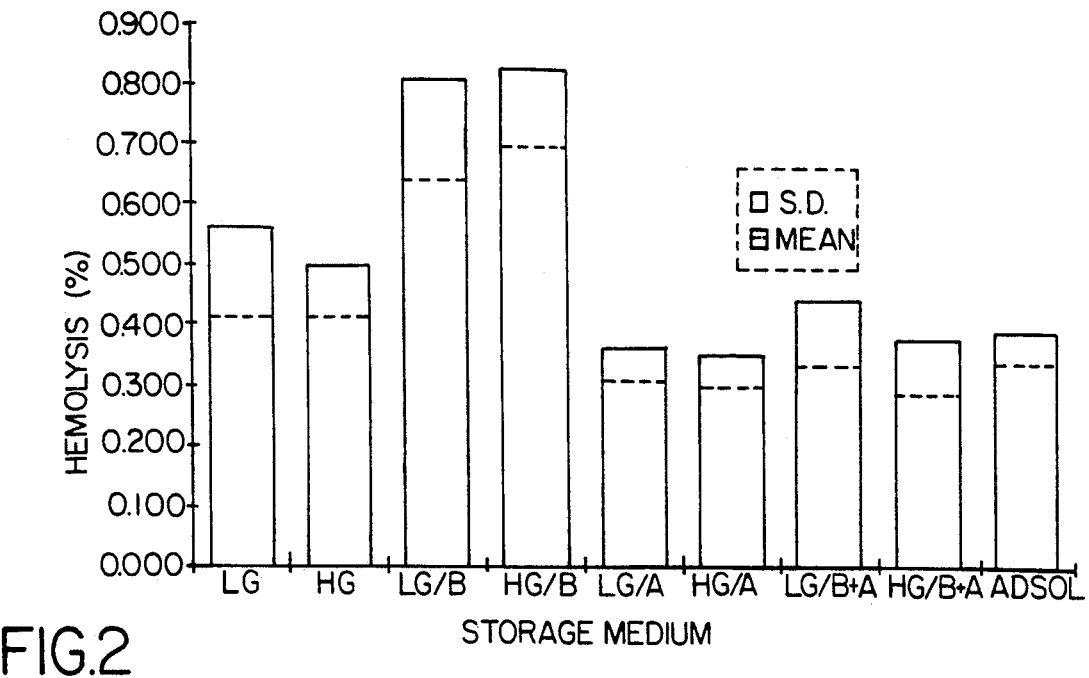
FIG. 2 graphically compares the percent of hemolysis of red blood cells after 49 days of storage in various embodiments of the red blood cell storage medium and a control storage medium.
Figure 3:
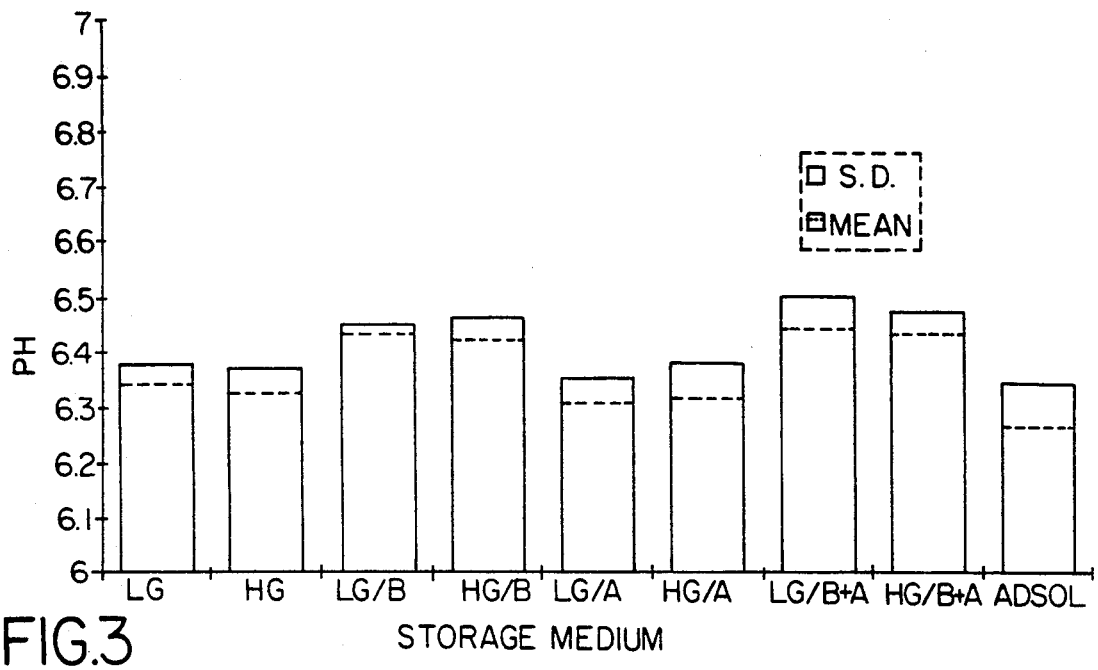
FIG. 3 graphically compares the pH of stored red blood cell in solution after 49 days of storage in various embodiments of the red blood cell storage medium.
Figure 4:
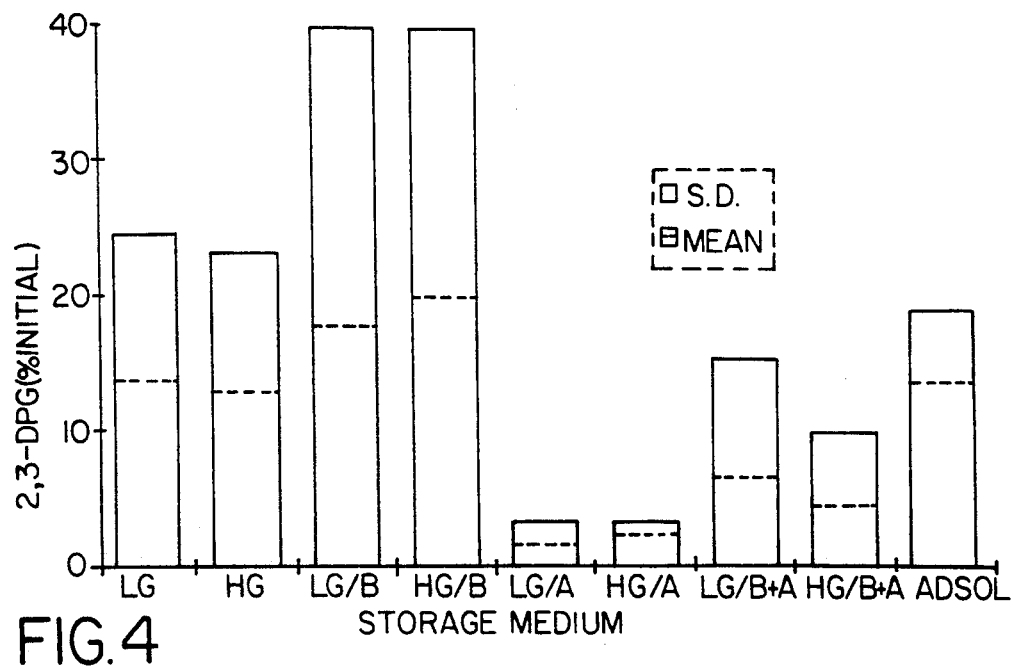
FIG. 4 graphically compares the percent loss of 2,3 DPG in red blood cells after 49 days of storage in various embodiments of the red blood cell storage medium and a control storage medium.

The results of these examples and comparative example as illustrated by FIGS. 1 and 2 demonstrate that red blood cells stored in the storage mediums fortified with sodium bicarbonate and adenine had superior ATP maintenance and less hemolysis after 49 days than the control red blood cells that were stored in the ADSOL ® brand storage medium. Suprisingly, good ATP levels were achieved with the red blood cell storage medium of this invention not having adenine. The results observed for these examples were slightly less than the results observed for the ADSOL ® medium.

The results of these examples and comparative example as illustrated by FIGS. 1 and 2 demonstrate that red blood cells stored in the storage medium fortified with sodium bicarbonate have desirably high pH levels and 2,3 DPG levels. No significant difference was observed between red blood cells stored in the storage medium of this invention with either low or high glucose concentrations when compared to red blood cells stored in the ADSOL ® brand storage medium.

These examples and comparative example demonstrate that the red blood cell storage medium of this invention fortified with both sodium bicarbonate and adenine produces desirable ATP maintenance during storage.

EXAMPLE 16 AND COMPARATIVE EXAMPLES K THORUGH O

The procedure used in Example 16 to separate red blood cells from whole blood and to make the storage medium are the same as those described above, but with a dextrose concentration of 7.0 grams per liter and a sodium bicarbonate concentration of 3 grams per liter. Comparative Examples L through O were not performed by the inventors, laboratory, but represent data reported by others.

The data of this example and comparative examples are derived from tests performed on whole blood units from 5 donors that were collected and processed according to standard blood bank methods. In the example the red blood cells were suspended in 100 milliters of the preferred embodiment of the platelet storage medium having a concentration of 270 milligrams per liter of adenine. The suspended red blood cells were stored in 600 milliliter Fenwal PL-146 primary plastic bags at 4° C. for up to 56 days. The results observed by this example and comparative examples are presented in Tables 22 and 23.

TABLE 22

| | | ATP uM/g of Hemoglobin | | | |
| | | DAYS OF STORAGE | | | |
| Example | MEDIUM | 35 | 42 | 49 | 56 |
|---|---|---|---|---|---|
| Ex. 16 | Platelet storage medium + adenine | 3.16 ± 0.58 | 2.88 ± 0.50 | 2.44 ± 0.52 | 2.26 ± 0.66 |
| C. Ex. K | ADSOL (Travenol)[2] | 3.15 ± 0.53 | 3.07 ± 0.40 | 2.44 ± 0.63 | 1.65 ± 0.27 |
| C. Ex. L | ADSOL (Travenol)[3] | not done | not done | 1.85 ± 0.52 | not done |
| C. Ex. M | AS-3 (Cutter)[3] | not done | 2.97 ± 0.51 | 1.80 ± 0.40 | not done |
| C. Ex. N | AS-3 (Cutter)[4] | not done | 2.27 ± 0.78 | 1.73 ± 0.46 | not done |
| C. Ex. O | SAGM (Terumo)[2] | not done | 2.44 ± 0.53 | not done | not done |

TABLE 23

| | | Hemolysis (% Hemoglobin in supernatant) | | | |
| | | DAYS OF STORAGE | | | |
| Example | MEDIUM | 35 | 42 | 49 | 56 |
|---|---|---|---|---|---|
| Ex. 16 | Platelet storage medium + adenine | 0.21 ± 0.10 | 0.37 ± 0.17 | 0.39 ± 0.22 | 0.70 ± 0.41 |
| C. Ex. K | ADSOL (Travenol)[2] | 0.29 ± 0.32 | 0.28 ± 0.07 | 0.39 ± 0.10 | 0.80 ± 0.32 |
| C. Ex. L | ADSOL (Travenol)[3] | not done | not done | 0.38 ± 0.19 | not done |
| C. Ex. N | AS-3 (Cutter)[4] | not done | 1.00 ± 0.21 | 1.08 ± 0.46 | not done |
| C. Ex. O | SAGM (Terumo)[2] | not done | 0.59 ± 0.46 | not done | not done |

[1] Experiments performed by inventors.
[2] Experimental data obtained from licensing studies performed by inventors' laboratory for Travenol, Inc. and Terumo, Inc., respectively.
[3] Experimental data reported in licensing studies for AS-3 (Cutter Biological) as reported in Transfusion 27:178, 1987 (Laboratory A).
[4] Experimental data reported in Licensing studies for AS-3 (Cutter Biological) as reported in Transfusion 27:178, 1987 (Laboratory B).

The results of this example and these comparative examples demonstrate that the red blood cell storage medium of this invention provides more desirable ATP levels and less hemolysis in red blood cells stored for more than 49 days than observed in red blood cells stored in other red blood cell storage mediums.

EXAMPLE 17

The procedures used in Example 17 to separate red blood cells from whole blood and to make the storage medium is the same as those described above.

The studies described as for Example 16 used the platelet storage medium with 3 grams per liter of sodium bicarbonate and PL-146 plastic containers. This resulted in a decrease in pH of the red blood cell solution to below 6.6 after 28 days of storage.

In Example 17 red blood cells are stored according to the procedure of Example 16, but Terumo XT-612 platelet containers made of thin polyvinylchloride (PVC) plastic and diethylhexylphthalate (DEHP) are used instead of PL-146 containers. Additionally, the red blood cells are stored with a 50 percent reduction in thickness when compared to the thickness of Example 16 and with an increased sodium bicarbonate concentration of 4 grams per liter. The red blood cell volumes used in the 400 milliliter Terumo XT-612 containers are two-thirds of the original volume. This is to provide the same ratio of red blood cell volume to container volume as used for the 600 milliliter PL-146 containers of Example 16.

Five studies were performed to discover whether or not the increased $CO_2$ permeability of the Terumo containers resulted in high pH levels and improved red blood cell qualities after storage. The 6.42±0.08 pH of the red blood cells stored in the Terumo XT-612 containers was only slightly higher than the 6.39±0.09 pH of the red blood cells stored in the PL-146 containers. Surprisingly, the red blood cells stored in the Terumo containers had improved ATP levels and less hemolysis during storage than did the red blood cells stored in the PL-146 containers. After 56 days of storage the mean ATP level was 2.54±0.57 umoles/gHb and hemolysis was 0.38±19 percent. This example demonstrates that prolonged storage of red blood cells in the storage medium of this invention is superior to the results obtained with other, commercially available preservation solutions. Furthermore, this example demonstrates that platelets and red blood cells can be stored in the same type of plastic containers.

We claim:

1. A sterile, plasma-free red blood cell storage medium comprising:
   a physiologically compatible, aqueous electrolyte solution, one liter of said electrolyte solution having:
   between about 3.0 grams and about 25.0 grams of dextrose;
   between about 3.0 grams and about 6.0 grams of sodium citrate; and
   between about 2.0 grams and about 4.2 grams of sodium bicarbonate;
   said red blood cell storage medium being isotonic and having a pH in a range of between about 6.8 and about 7.4, said red blood cell storage medium being capable of preserving red blood cells for at least about 49 days at a temperature of at least about 4° C.

2. The red blood cell storage medium according to claim 1 further comprising citric acid, said citric acid being in a concentration of 1 liter of said red cell storage medium of about 0.51 gram and said dextrose being in a concentration of about 7.035 grams, said sodium citrate being in a concentration of about 4.471 grams, and said sodium bicarbonate being in a concentration of about 3.0 grams.

3. The red blood cell storage medium according to claim 1 wherein one liter of said electrolyte solution has electrolytes including:
   between about 6.4 grams and about 7.6 grams of sodium chloride;
   between about 0.2 gram and about 0.4 gram of potassium chloride;
   between about 0.1 gram and about 0.4 gram of calcium chloride;
   between about 0.2 gram and about 0.4 gram of magnesium sulphate; and
   between about 0.1 gram and about 0.6 gram of monobasic sodium phosphate.

4. The red blood cell storage medium according to claim 3 wherein said electrolytes include:
   about 6.45 grams of sodium chloride;
   about 0.375 gram of potassium chloride;
   about 0.248 gram of calcium chloride;
   about 0.2 gram of magnesium sulphate; and
   about 0.355 gram of monobasic sodium phosphate.

5. The red blood cell storage medium according to claim 4 further comprising citric acid, said citric acid being in a concentration of 1 liter of said red cell storage medium of about 0.51 gram and said dextrose being in a concentration of about 7.2 grams, said sodium citrate being in a concentration of about 4.471 grams, and said sodium bicarbonate being in a concentration of about 3.0 grams.

6. The red blood cell storage medium according to claim 5 further comprising a human red blood cell concentrate.

7. The red blood cell storage medium according to claim 1 wherein said electrolytes include:
   between about 0.26 gram and about 0.30 gram of adenine.

8. The red blood cell storage medium according to claim 7 wherein said electrolytes include:
   about 0.30 gram of adenine.

9. A process for preserving red blood cells in a sterile, plasma-free red blood cell storage medium comprising:
   preparing a physiologically compatible, aqueous electrolyte solution, one liter of said electrolyte solution having:
   between about 0.26 gram and about 0.30 gram of adenine;
   between about 3.0 grams and about 25.0 grams of dextrose;
   between about 3.0 grams and about 6.0 grams of sodium citrate; and
   between about 2.0 grams and about 4.2 grams of sodium bicarbonate;
   suspending red blood cells in said red blood cell storage medium, said red blood cell storage medium being isotonic and having a pH in a range of between about 6.8 and about 7.4, whereby a substantial concentration of said red blood cells remain viable for at least about 49 days at a temperature of at least about 4° C.

10. The process for preserving red blood cells according to claim 9 wherein said red blood cell storage medium includes citric acid, said citric acid being in a concentration of 1 liter of said red cell storage medium of about 0.51 gram and said dextrose is in a concentration of about 7.2 grams, said sodium citrate is in a concetration of about 4.471 grams, and said sodium bicarbonate is in a concentration of about 3.0 grams.

11. The process for preserving red blood cells according to claim 10 wherein one liter of said electrolyte solution has electrolytes including:
   between about 6.4 grams and about 7.6 grams of sodium chloride;
   between about 0.2 gram and about 0.4 gram of potassium chloride;
   between about 0.1 gram and about 0.4 gram of calcium chloride;
   between about 0.2.gram and about 0.4 gram of magnesium sulphate; and
   between about 0.1 gram and about 0.6 gram of monobasic sodium phosphate.

12. The process for preserving red blood cells according to claim 11 wherein said electrolytes include:
   about 6.45 grams of sodium chloride;
   about 0.375 gram of potassium chloride;
   about 0.248 gram of calcium chloride;
   about 0.2 gram of magnesium sulphate; and
   about 0.355 gram of monobasic sodium phosphate.

13. A product of the process according to claim 9.

14. A product of the process according to claim 12.

* * * * *